United States Patent [19]

Sands

[11] 4,114,198
[45] Sep. 19, 1978

[54] WELDER'S HELMET LENS

[76] Inventor: Jessie E. Sands, 1719 Maple St., Russell, Kans. 67665

[21] Appl. No.: 781,527

[22] Filed: Mar. 25, 1977

[51] Int. Cl.$^2$ .............................................. A61F 9/06
[52] U.S. Cl. ............................................. 2/8; 2/427
[58] Field of Search ............... 2/8, 427, 430, 432, 2/9, 11; D2/233, 234

[56] References Cited

U.S. PATENT DOCUMENTS

| 2,395,053 | 2/1946 | Landis | 2/8 |
| 2,583,304 | 1/1952 | Pipher | 2/8 UX |
| 3,298,031 | 1/1967 | Morgan | 2/427 X |
| 3,311,922 | 4/1967 | Bezzerides | 2/8 |

FOREIGN PATENT DOCUMENTS

| 519,567 | 3/1931 | Fed. Rep. of Germany | 2/8 |
| 1,190,765 | 5/1970 | United Kingdom | 2/8 |

*Primary Examiner*—Peter Nerbun
*Attorney, Agent, or Firm*—Clarence A. O'Brien; Harvey B. Jacobson

[57] ABSTRACT

A generally conventional welders' shield is provided including a support frame for placement over and support from the upper portion of a welder's head and a rearwardly opening upstanding shield body pivotally supported from opposite side portions of the frame. The shield body includes a viewing aperture therein to be in horizontal registry with the eyes of the wearer of the frame when the shield body is in an upstanding position and the upper margin of the viewing aperture is at an elevation to be at least horizontally aligned with straight forward vision of the eyes of the wearer of the frame. The lower margin of the viewing aperture includes opposite side portions depressed downwardly sufficiently to provide unobstructed vision of the wearer when the latter is viewing through the lower portions of bifocal glasses and the center portion of the lower margin of the viewing aperture is upwardly displaced relative to the depressed opposite side portions of the lower margin to be positioned above the nostril level of the wearer. Further, a light filtering panel is removably secured over the viewing aperture.

3 Claims, 6 Drawing Figures

WELDER'S HELMET LENS

BACKGROUND OF THE INVENTION

There are many instances wherein a welder performs welding operations in cold climates. Conventional welding shields are provided with viewing apertures which allow generally straight forward vision of a welder, but the lower margin of the viewing aperture is not sufficiently depressed downwardly to enable a welder who wears bifocal glasses to view his work in an unobstructed manner through the lower portions of his bifocal lenses. As a result, the welder must pivot his shield downwardly in order that the lower marginal edge of the viewing aperture may be sufficiently depressed to enable him to view his work through the lower portions of his bifocals. While this is not very troublesome in warm climates, downward pivoting of a shield in this manner by a welder wearing bifocal glasses in cold climates results in the viewing window being downwardly displaced into registry with the air being exhaled through the welder's nostrils. Inasmuch as air being exhaled is quite moist, the warmer content of the exhaled air tends to condense on the inner surface of the light filtering panel. Of course, condensation on the inner surface of the light filtering panel severely limits the vision of the welder.

Although some welding helmets are provided with viewing apertures whose lower marginal edges are sufficiently depressed to enable welders wearing the helmets to view their welding operation through the lower portions of bifocal lenses worn by the welder, these vertically elongated viewing windows are also subjected to the formation of condensation on the inner surfaces thereof in cold climates due to moist air being exhaled from the nostrils of the welder.

Accordingly, a need exists for an improved viewing window in a welder's helmet which will enable a welder to view close welding operations through the lower portions of bifocal lenses worn by the welder and without lower portions of the viewing window of the helmet being in registry with moist air being exhaled from the nostrils of the welder.

Examples of conventional and slightly modified welder's helmets including some of the general structural and operational features of the instant invention are disclosed in U.S. Pat. Nos. 2,103,006, 2,487,848, 2,598,265, 2,628,530, 2,668,951, 2,784,410, 2,817,087 and 2,973,522.

BRIEF DESCRIPTION OF THE INVENTION

The welder's helmet of the instant invention is equipped with a viewing aperture closed by a light filtering panel and including opposite side lower marginal portions depressed downwardly relative to the central lower marginal portion of the viewing aperture. The downwardly depressed opposite side lower marginal portions of the viewing aperture enable the associated welder to view close welding work through the lower portions of bifocal lenses and the relatively elevated central lower marginal portion of the viewing aperture insures that no portion of the viewing aperture will be in registry with moist air exhaled through the nostrils of the wearer of the helmet or condensing on the inner surface of the light filtering panel which closes the viewing aperture.

The main object of this invention is to provide a welder's helmet constructed in a manner whereby a welder wearing the helmet may view close welding work through the lower portions of bifocal lenses.

Another object of this invention is to provide a welder's helmet in accordance with the preceding object and constructed in a manner whereby the viewing aperture of the helmet will be devoid of portions thereof in registry with moist air being exhaled from the nostrils of an associated welder.

Yet another object of this invention is to provide an improved viewing window for welder's helmets which may be readily incorporated into welders' helmets being presently manufactured.

A final object of this invention to be specifically enumerated herein is to provide a welder's helmet in accordance with the preceding objects and which will conform to conventional forms of manufacture, be of simple construction and easy to use so as to provide a device that will be economically feasible, long lasting and relatively trouble free in operation.

These, together with other objects and advantages which will become subsequently apparent, reside in the details of construction and operation as more fully hereinafter described and claimed, reference being had to the accompanying drawings forming a part hereof, wherein like numerals refer to like parts throughout.

DETAILED DESCRIPTION OF THE INVENTION

Figure 1:
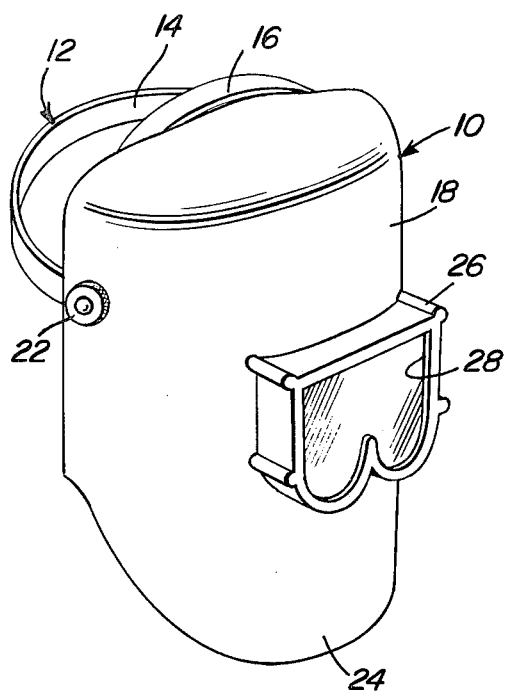
FIG. 1 is a perspective view of a welder's helmet constucted in accordance with the present invention.

Referring now more specifically to the drawings, the numeral 10 generally designates the improved welder's helmet of the instant invention. The helmet 10 includes a frame referred to in general by the reference numeral 12 and including a head encircling band 14 and an upper downwardly opening generally semi-cylindrical upper band 16 whose lower ends are anchored to opposite side portions of the head encircling band 14. The helmet 10 further includes an upstanding shield body 18 defining a rearwardly opening cavity 20 in which the forward portion of the frame 12 is received. The shield body 18 is pivotally supported as at 22 from opposite side portions of the frame 12 and the shield body 18 may be pivoted from the upstanding position thereof illustrated in FIG. 1 of the drawings to rearwardly and upwardly inclined position with the lower skirt portion 24 of the shield body 18 out of registry with forward vision of the wearer of the helmet 10.

The shield body 18 includes a generally vertically centered mounting boss 26 having a viewing aperture 28 formed therein. A light filtering panel 30 is secured within the mounting boss 26 by means of removable springs 32 and thus may be replaced whenever desired.

Figure 5:
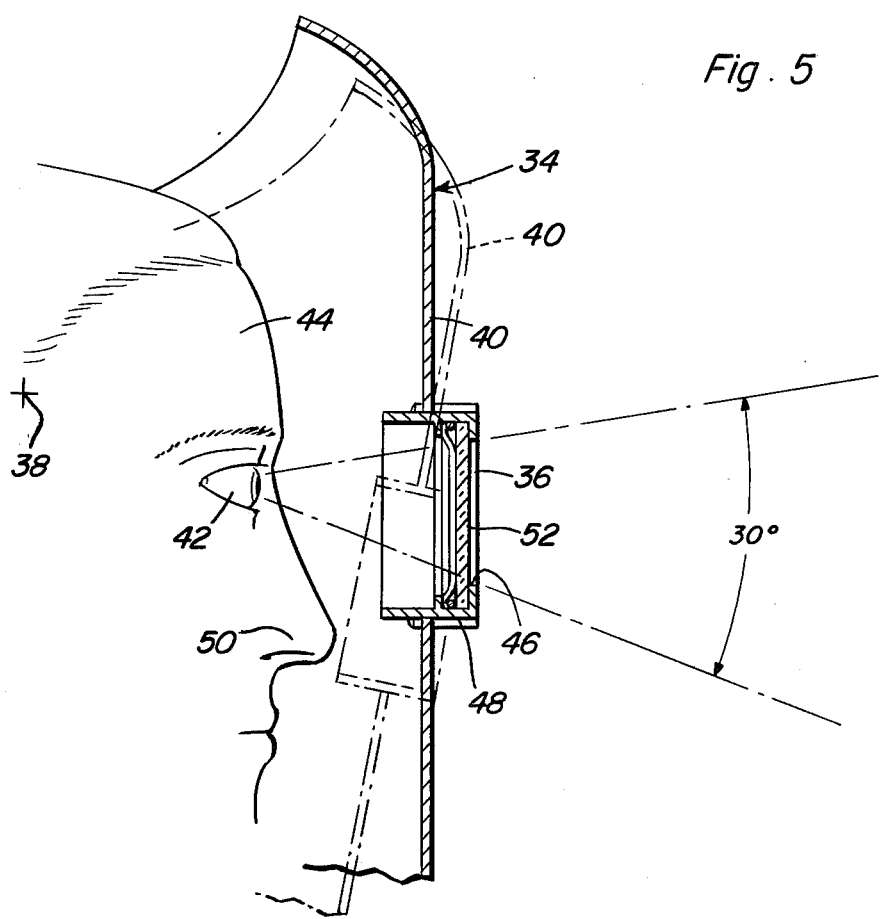
FIG. 5 is a vertical sectional view of a conventional form of a welder's helmet in position as worn on the head of a welder and illustrating the usual position of the helmet in solid lines and a downwardly and rearwardly pivoted position of the conventional helmet which is necessary in the event the welder wishes to view close welding work through the lower portions of bifocals worn by the welder.

With attention now invited more specifically to FIG. 5 of the drawings, there may be seen a conventional form of welder's helmet referred to in general by the reference numeral 34. The welder's helmet 34 is substantially similar to the helmet 10, except that the viewing aperture 36 thereof is substantially rectangular in configuration.

The conventional helmet 34 is mounted from the associated frame (not shown) corresponding to the frame 12 for oscillation about a horizontal transverse axis 38 relative to the associated frame. When the shield body 40 of the conventional helmet 34 is vertically disposed, it may be seen that the forward positioning of the viewing aperture 36 relative to the eyes 42 of the wearer 44 limits the vertical field of vision of the welder 44 to approximately 30°. Further, it may be readily appreciated from FIG. 5 of the drawings that if the wearer 44 was wearing bifocal glasses he could not view close welding work through the lower portion of his bifocal lenses with the shield body 40 of the conventional helmet 34 in the vertical position thereof illustrated in phantom lines in FIG. 5. Accordingly, it is the practice of welders who wear bifocal lenses to forwardly and downwardly pivot the shield body 40 to the position thereof illustrated in phantom lines in FIG. 5 of the drawings in order that the lower marginal edge 46 of the viewing window 36 will be sufficiently depressed in order to enable the user 44 to view close welding work through the lower portion of his bifocal lenses. However, forward and downward pivoting of the shield body 40 relative to the associated frame corresponding to the frame 12 results in the lower marginal portion of the boss 48 corresponding to the boss 26 being registered with the moist air being exhaled from the nostrils 50 of the user 44. This, of course, results in condensation forming on the inner surface of the light filtering panel 52 corresponding to the panel 30 when the user 44 is welding in cold climates.

Figure 2:
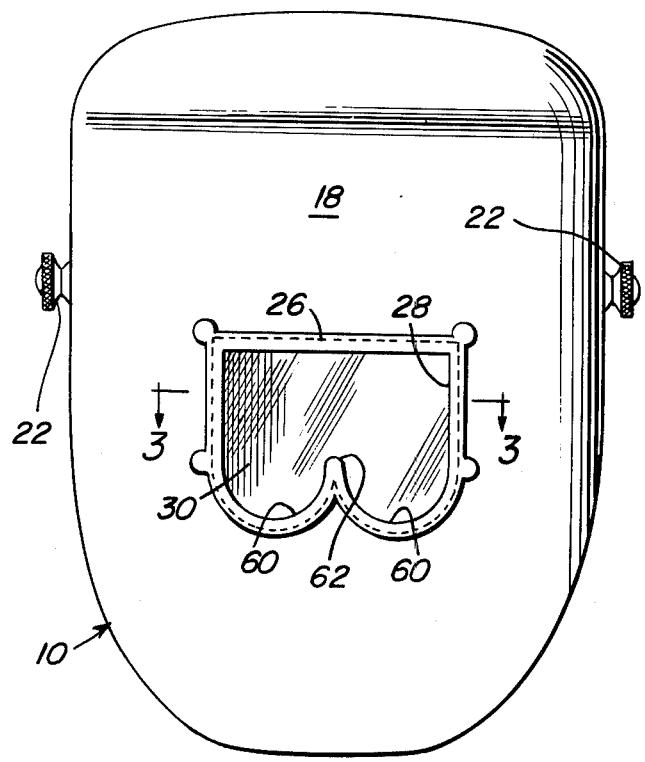
FIG. 2 is an enlarged front elevational view of the welder's helmet.
Figure 3:
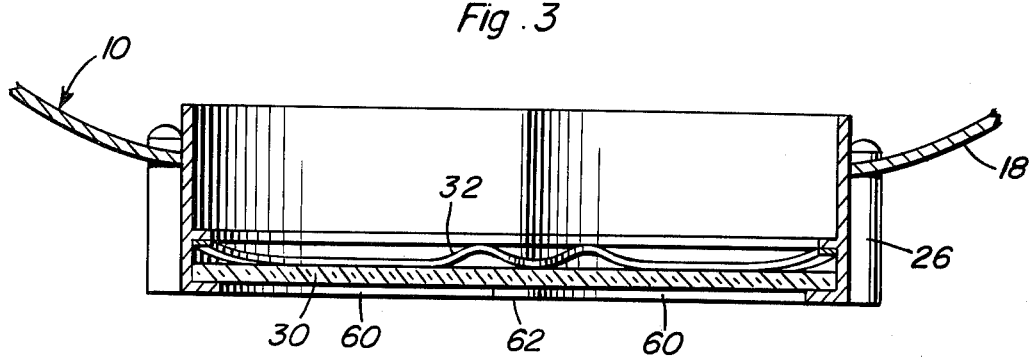
FIG. 3 is an enlarged fragmentary horizontal sectional view taken substantially upon the plane indicated by the section line 3—3 of FIG. 2.
Figure 4:
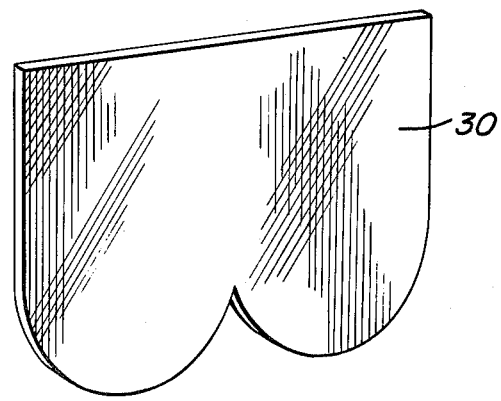
FIG. 4 is an enlarged perspective view of the light filtering panel which closes the viewing aperture of the helmet.
Figure 6:
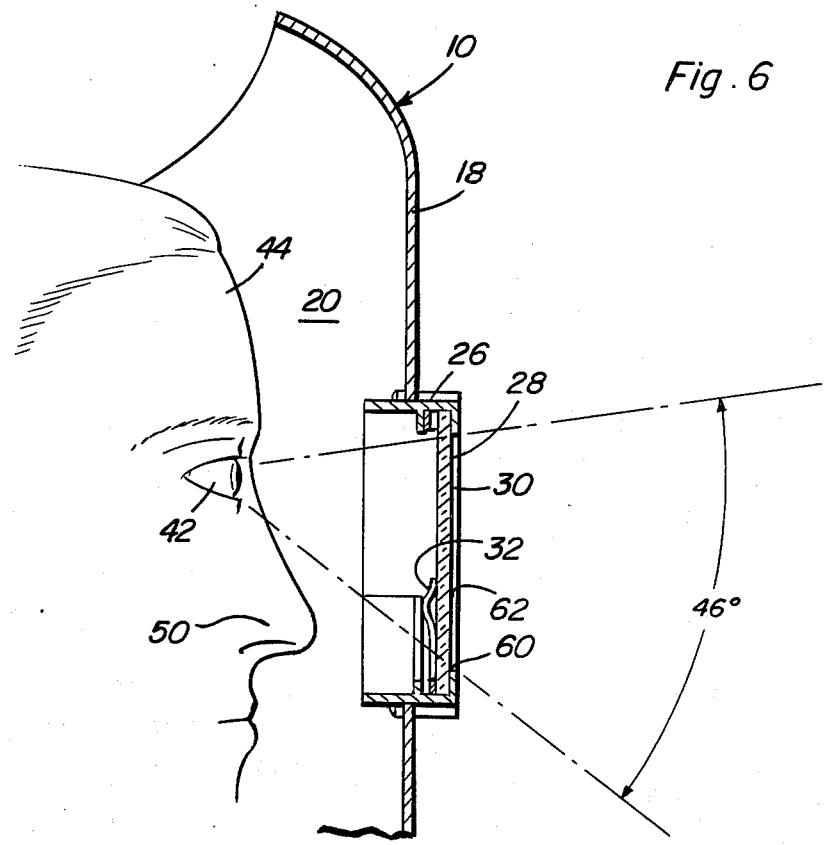
FIG. 6 is a vertical sectional view similar to FIG. 5 but illustrating the helmet of the instant invention and the manner in which the user of the helmet of the instant invention is afforded a more depressed forward field of vision but with the viewing aperture of the helmet out of registry with air being exhaled through the nostrils of the welder.

With attention now invited more specifically to FIG. 6 of the drawings, it may be seen that the shield body 18 is positioned in substantially the same manner relative to the user 44 but that the viewing aperture 28 includes opposite side lower marginal portions 60 which are sufficiently low in elevation relative to the eyes 42 of the wearer 44 to afford the wearer 44 a vertical range of vision of approximately 46° or 1½ times the 30° vertical range of vision of the user 44 utilizing the helmet 34. In addition, it may be seen from FIGS. 2 and 6 of the drawings that the viewing aperture 28 includes a central lower marginal portion 62 which is at substantially the same relative elevation as the lower marginal portion 46 of the viewing aperture 36. Accordingly, while the wearer 44 may view close welding work through the lower portions of bifocal glasses worn by the user 44, the central lower marginal portion 62 of the viewing aperture 28 is sufficiently elevated to be clearly out of registry with air being exhaled through the nostrils 50 of the user 44. In addition, inasmuch as the mounting boss 26 and the adjacent portions of the shield body 18 are maintained a greater distance spaced forwardly of the forward extremities of the face of the user 44, additional space is provided for air circulation between the shield body 18 and the face of the user 44. Accordingly, the formation of condensation on the inner surface of the light filtering panel or lense 30 is eliminated, even when the helmet 10 is used in cold climates.

The opposite side lower marginal portions 60 of the viewing aperture 28 are generally semi-circular and open upwardly. Accordingly, from FIG. 2, it may be seen that the opposite side lower marginal portions 60 are spaced below the normal position of the lower marginal edge 46 of the viewing aperture 36 a distance slightly less than ¼ of the entire horizontal width of the viewing aperture 28. This additional vertical extent of the opposite side portions of the viewing aperture 28 is sufficient to increase the vertical range of the vision of the wearer 44 downwardly by approximately 50%.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A protective guard for welders, said guard including a support frame for placement over and support from the upper portion of a welder's head, said frame including opposite side portions, a rearwardly opening upstanding shield, means pivotally supporting said shield from said opposite side portions for angular displacement relative to said frame about a horizontal transverse axis and with at least the forward portion of said frame disposed within said rearwardly opening shield, said shield being oscillatable relative to said frame between an upstanding position and a rearwardly and upwardly inclined position with the upper portion of said shield swung rearwardly and upwardly and the lower portion of said frame swung forwardly and upwardly, said shield including aperture defining means defining a viewing aperture therein below the level of said axis when said shield is in said upstanding position and to be disposed forwardly of the wearer's face and in horizontal registry with the eyes of the wearer of said frame when said shield is in said upstanding position, the upper margin of said viewing aperture being at an elevation to be at least horizontally aligned with straight forward vision of the eyes of said wearer, the portion of said aperture defining means defining the lower margin of said viewing aperture including opposite side portions depressed downwardly sufficiently to provide unobstructed vision of said wearer when the latter is viewing through the lower portions of bifocal glasses and a central portion upwardly displaced relative to said depressed opposite side portions to be positioned above the nostril level of said wearer as well as forward of the nose of the wearer, and a light filtering panel closing said aperture, said aperture defining means being mounted from said shield for positioning forwardly of the face of the user to facilitate free circulation of air within said shield adjacent the nose and eyes of the wearer.

2. The combination of claim 1 wherein said opposite side lower marginal portions define upwardly opening arcuate marginal portions.

3. The combination of claim 1 wherein said aperture defining means includes a mounting portion surrounding said aperture, said light filtering panel being removably supported from said mounting portion.

* * * * *